United States Patent [19]
Yokoi et al.

[11] Patent Number: 5,703,064
[45] Date of Patent: Dec. 30, 1997

[54] PESTICIDAL COMBINATIONS

[75] Inventors: Shinji Yokoi; Akira Nishida, both of Shiga-ken; Tokio Obata; Kouichi Goka, both of Ube, all of Japan

[73] Assignees: Sankyo Company, Limited, Tokyo; Ube Industries Ltd., Ube, both of Japan

[21] Appl. No.: 405,795

[22] Filed: Mar. 16, 1995

[30] Foreign Application Priority Data

Mar. 16, 1994 [JP] Japan ............................ HEI6-045405

[51] Int. Cl.$^6$ ............................ A01N 43/54; A01N 57/00
[52] U.S. Cl. ............................ 514/80; 514/256
[58] Field of Search ............................ 514/80, 256

[56] References Cited

U.S. PATENT DOCUMENTS

| | | | |
|---|---|---|---|
| 4,374,833 | 2/1983 | Badmin et al. | 424/225 |
| 4,845,097 | 7/1989 | Matsumoto et al. | 514/234.2 |
| 4,935,516 | 6/1990 | Ataka et al. | 544/319 |
| 4,982,008 | 1/1991 | Ataka et al. | 568/592 |
| 4,985,596 | 1/1991 | Ataka et al. | 564/258 |
| 5,120,721 | 6/1992 | Morimoto et al. | 514/103 |

FOREIGN PATENT DOCUMENTS 0 196 524  10/1986  European Pat. Off. .

OTHER PUBLICATIONS

Worthing et al, The Pesticide Manual, 9th Ed. (1991), pp. 747 and 748.

L.C. Gaughan et al, "Pesticide interactions: effects of organophosphorus pesticides on the metabolism, toxicity, and persistence of selected pyrethroid insecticides", Chemical Abstracts, vol. 94, No. 9, 1981, No. 59740k of Pestic. Biochem. Physio., vol. 14, No. 1, 1980, pp. 81–85.

I. Ishaaya et al, "Cypermethrin synergism by pyrethroid esterase inhibitors in adults of the whitefly Bemisia tabaci", Chemical Abstracts, vol. 107, No. 9, 1987, No. 72818y of Pestic Biochem. Physiol., vol. 28, No. 2, 1987, pp. 155–162.

Primary Examiner—Allen J. Robinson
Attorney, Agent, or Firm—Frishauf, Holtz, Goodman, Langer & Chick, P.C.

[57] ABSTRACT

Combinations of the known compound pyrimidifen with phosphorus-containing pesticides have a synergistic pesticidal effect, especially against mites.

3 Claims, No Drawings

PESTICIDAL COMBINATIONS

BACKGROUND OF THE INVENTION

The present invention relates to combinations of the known pesticide pyrimidifen with other phosphorus-containing pesticides.

EP-A-196,524 discloses a large number of phenoxyalkylaminopyrimidine derivatives in the context of insecticides and acaricides. One of these compounds, 5-chloro-N-{2-[2,3-dimethyl-4-(2-ethoxyethyl)phenoxy]-ethyl}-6-ethyl-4-pyrimidinamine, also known as pyrimidifen (compound no. 75 in Table 1 of EP-A-196,524), is demonstrated as having good insecticidal and acaricidal activity. The formula of pyrimidifen is as follows:

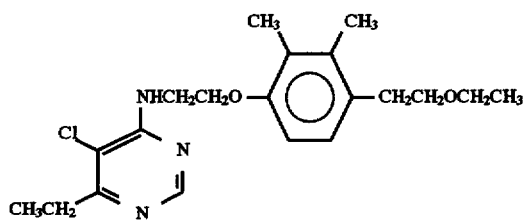

Phosphorus-containing pesticides are well known in the art, and the art also provides well known methods for the production of further such compounds where they are not known per se. EP-A-196,524 also discloses a lengthy list of possible insecticides and fungicides which may be used in combination with the claimed phenoxyalkylaminopyrimidines, and states that "in some cases, a synergistic effect may be expected", but fails to provide any justification for this statement.

Spider mites are a significant crop pest, worldwide. To this end, many groups have attempted to find suitable pest control agents. Many agents have been found, but the efficacy of such agents tends to be rather short-lived, owing to the development of resistance to newly introduced cidal agents. In areas of heavy cultivation, it is often the case that the mite population is resistant to a large number of chemicals. In this respect, some mites are even developing resistance to pyrimidifen, one of the newest miticidal agents.

BRIEF SUMMARY OF INVENTION

Surprisingly, we have now discovered that a combination of pyrimidifen with one or more phosphorus-containing pesticides has a surprisingly potent synergistic effect, especially against spider mites, even where resistance to pyrimidifen has developed.

Thus, in a first aspect, the present invention provides a pesticidal composition comprising 5-chloro-N-{2-[2,3-dimethyl-4-(2-ethoxyethyl)phenoxy]-ethyl}-6-ethyl-4-pyrimidinamine (hereinafter referred to as pyrimidifen) together with one or more compounds having the general formula:

(I)

[wherein X represents an oxygen atom or a sulfur atom;

Y represents an oxygen atom, a sulfur atom or a single bond;

$R^1$ represents an alkyl group having from one to six carbon atoms;

$R^2$ represents an alkoxy group having from one to eight carbon atoms, an alkylthio group having from one to eight carbon atoms, an alkylcarbonylamino group having from one to four carbon atoms or a phenyl group; and $R^3$ represents an alkyl group having from one to eight carbon atoms, an alkenyl group having from two to six carbon atoms, an amino group, a phenyl group or a heteroaryl group, and is unsubstituted or is substituted with one, two or three substituents which may be the same or different and which are selected from the group (A) consisting of:

halogen atoms, phenyl groups, nitro groups, cyano groups, oxo groups, alkyl groups having from one to eight carbon atoms, alkoxy groups having from one to eight carbon atoms, aliphatic acyl groups having from one to six carbon atoms, alkoxycarbonyl groups having from one to six carbon atoms, alkylthio groups having from one to six carbon atoms, alkylamino groups having from one to six carbon atoms, dialkylamino groups wherein each alkyl is the same or different and each has from one to six carbon atoms, heteroaryl groups, carbamoyl groups, alkylcarbamoyl groups wherein the alkyl part has one to six carbon atoms, and heterocyclyl groups which are unsubstituted or are substituted with one, two or three substituents selected from group A, other than heterocyclyl groups, or $R^3$ represents a group of formula

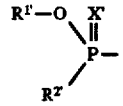

wherein $R^{1'}$, $R^{2'}$ and $X'$ are respectively selected from the groups defined above for $R^1$, $R^2$ and X] for use in agriculture or horticulture.

DETAILED DESCRIPTION OF INVENTION

Preferred compounds of formula (I) for use in the formulations of the present invention are those compounds known as isoxathion, diazinon, prothiofos, methidathion, thiometon, malathion, quinalphos, dimethoate, chlorpyrifos, profenofos, monocrotophos and ethion, the systematic names of which are given hereinunder. Of the above compounds, dimethoate, chlorpyrifos, profenofos, monocrotophos and ethion are particularly preferred.

In an alternative aspect, the present invention provides a pesticidal composition comprising pyrimidifen and at least one of profenofos, monocrotophos and ethion.

The present invention further provides vegetative reproductive material, especially seeds, treated with the compositions of the invention; and methods of treating such material with the compositions of the present invention.

The present invention further provides a method for the treatment of an agricultural or horticultural area against non-mammalian, non-arian and non-reptilian pests comprising the administration thereto of an effective amount of a composition comprising pyrimidifen and one or more compounds of formula (I).

It will be appreciated that the compositions of the present invention do not necessarily have to be administered as a combination, and that they may be provided as separate ingredients and even administered separately, provided that the active ingredients are present together in situ.

While it is possible to use two or more compounds of formula (I) in the compositions of the present invention, it is generally preferred to use only one compound of formula (I), generally for reasons of convenience and cost.

It will be appreciated that the term "pesticidal", as used herein, is used in the context of non-mammalian, non-reptilian and non-arian pests. Pests against which the compositions of this invention are particularly useful are mites, especially spider mites, but those skilled in the art will appreciate that the compositions of the present invention may also be used as insecticides and cidal agents for crustacea and the like. It is a particular advantage of the present invention that the compositions which are provided are useful against spider mite populations insensitive to pyrimidifen.

In the definitions of $R^1$ and $R^{1'}$ in the compounds of general formula (I), alkyl groups having from one to six carbon atoms may suitably be selected from straight or branched chain alkyl groups such as, for example; the methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, particularly the methyl and ethyl groups.

In the definitions of $R^2$ and $R^{2'}$ and substituent group A in the compounds of general formula (I), alkoxy groups having from one to eight carbon atoms may suitably be selected from straight or branched chain alkoxy groups such as, for example; the methoxy, ethoxy, n-propoxy, isopropoxy, n-butoxy, isobutoxy, s-butoxy, tert-butoxy, n-pentyloxy, isopentyloxy, 2-methylbutyloxy, neopentyloxy, n-hexyloxy, 4-methylpentyloxy, 3-methylpentyloxy, 2-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy, n-heptyloxy and n-octyloxy groups, particularly the methoxy and ethoxy groups.

In the definitions of $R^3$ and substituent group A in general formula (I), alkyl groups having from one to eight carbon atoms may suitably be selected from straight or branched chain alkyl groups, such as those exemplified above with respect to $R^1$, as well as, for example, the n-heptyl and n-octyl groups.

In the definition of $R^2$ and $R^{2'}$ in the compounds of general formula (I), alkylthio groups having from one to eight carbon atoms may suitably be selected from straight or branched chain alkylthio groups wherein the alkyl groups are as exemplified hereinabove with respect to $R^1$, $R^3$ and A.

In the definitions of $R^2$ and $R^{2'}$ in general formula (I), alkylcarbonylamino groups having from one to four carbon atoms may suitably consist of a carbonylamide group combined with a straight or branched chain alkyl group having 1 to 4 carbon atoms, such as, for example; the methylcarbonylamide, ethylcarbonylamide, n-propylcarbonylamide, isopropylcarbonylamide, n-butylcarbonylamide, isobutylcarbonylamide, s-butylcarbonylamide and tert-butylcarbonylamide groups.

In the definition of $R^3$ in general formula (I), alkenyl groups having from two to six carbon atoms may suitably be selected from straight or branched chain alkenyl groups such as, for example; the vinyl, allyl, 1-propenyl, 1-methyl-2-propenyl, 2-methyl-1-propenyl, 2-methyl-2-propenyl, 2-ethyl-2-propenyl, 1-butenyl, 2-butenyl, 1-methyl-2-butenyl, 2-methyl-2-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups, particularly the vinyl and allyl groups.

In the definitions of $R^3$ and substituent group A in general formula (I), heteroaryl groups may suitably be selected from 5- to 8-membered mono-, bi- or tricyclic heterocyclic groups having from one to five hetero-atoms which may be the same or different and selected from oxygen, sulfur and nitrogen atoms. Suitable examples of heteroaryl groups include; the furanyl, thienyl, pyrrolyl, oxazolyl, isoxazolyl, thiazolyl, thianyl, pyridyl, pyridazinyl, pyrimidinyl, pyrazolyl, imidazolyl, triazinyl, thiadiazolyl, imidazothiazolyl, benzisoxazolyl, chromenyl, quinolinyl, benzothianyl, quinoxalinyl and benzotriazinyl groups.

In the definition of substituent group A in general formula (I), aliphatic acyl groups may suitably be selected from straight or branched chain aliphatic acyl groups such as, for example; the formyl, acetyl, propionyl, butyryl and valeryl groups.

In the definition of substituent group A in general formula (I), alkoxycarbonyl groups having from one to six carbon atoms may suitably be selected from straight or branched chain alkoxycarbonyl groups such as, for example; the methoxycarbonyl, ethoxycarbonyl, propoxycarbonyl, butoxycarbonyl, isobutoxycarbonyl and tert-butoxycarbonyl groups.

In the definition of substituent group A in general formula (I), alkylthio groups having from one to six carbon atoms may suitably be selected from straight or branched chain alkylthio groups such as, for example, the methylthio, ethylthio, propylthio and butylthio groups.

In the definition of substituent group A in general formula (I), alkylamino groups having from one to six carbon atoms may suitably consist of an amino group combined with a straight or branched chain alkyl group having 1 to 6 carbon atoms. Suitable alkyl groups are as defined above with respect to $R^1$. Examples of suitable alkylamino groups include the methylamino, ethylamino, propylamino, butylamino, pentylamino and hexylamino groups.

In the definition of substituent group A in general formula (I), dialkylamino groups may suitably consist of an amino group combined with two straight or branched chain alkyl groups which may be the same or different, each having 1 to 6 carbon atoms. Suitable examples of such dialkyl amino groups include the dimethylamino, diethylamino, methyethylamino, dipropylamino and dibutylamino groups.

In the definition of substituent group A in general formula (I), suitable halogen atoms include the fluorine, chlorine, bromine and iodine atoms, especially the chlorine and fluorine atoms, particularly the chlorine atom.

In the definition of substituent group A in general formula (I), heterocycyl groups may be saturated, unsaturated or partially saturated, and may suitably be selected from 5 or 6-membered heterocyclic groups having from one to five hetero-atoms which may be the same or different and selected from oxygen, sulfur and nitrogen atoms. Suitable examples of heterocycyl groups include; the tetrahydropyranyl groups, which may be substituted or unsubstituted, such as the tetrahydropyran-2-yl, 3-bromotetrahydropyran-2-yl and 4-methoxytetrahydropyran-4-yl groups; tetrahydrothiopyranyl groups, which may be substituted or unsubstituted, such as the tetrahydrothiopyran-2-yl and 4-methoxytetrahydrothiopyran-4-yl groups; tetrahydrofuranyl groups, which may be substituted or unsubstituted, such as the tetrahydrofuran-2-yl group; tetrahydrothienyl groups, which may be substituted or unsubstituted, such as the tetrahydrothien-2-yl group; thiadiazolyl groups, such as 5-methoxy-2-oxo-2,3-dihydro-1,3,4-thiadiazol-3-yl; the furanyl, thienyl, pyrrolyl, oxazolyl, isoxazolyl, thiazolyl, thianyl, pyridyl, pyridazinyl, pyrimidinyl, pyrazolyl, imidazolyl, triazinyl, thiadiazolyl, imidazothiazolyl, benzisoxazolyl, chromenyl, quinolinyl, benzothianyl, quinoxalinyl, benzotriazinyl groups.

In the definition of substituent group A in general formula (I), suitable alkyl groups in the definition of alkylcarbamoyl are as defined above with respect to $R^1$.

Organic phosphates represented by the general formula (I) include many well-known compounds, such as the insecticides; 2,2-dichlorovinyl phosphate (dichlorvos), dimethyl-2,2,2-trichloro-1-hydroxyethyl phosphonate (trichlorfon), O,O-dimethyl-S-(2,3-dihydro-5-methoxy-2-oxo-1,3,4-thiadiazol-3-ylmethyl) phosphorodithioate (methidathion), O,O-dimethyl-O-(3-methyl-4-nitrophenyl) thiophosphate (fenitrothion), O-2,4-dichlorophenyl-O-ethyl-S-propyl phosphorodithioate (prothiofos), O,O-dipropyl-O-4-methylthiophenyl phosphate (propaphos), O-4-bromo-2-chlorophenyl-O-ethyl-S-propyl phosphorothioate (profenofos), 3-(O,O-diethoxythiophosphorylthiomethyl)-6-chlorobenzoxazolone (phosalone), O,O-dimethyl-S-(N-formyl-N-methylcarbamoylmethyl) phosphorodithioate (formothion), S-1,2-bis(ethoxycarbonyl)ethyl-O,O-dimethyl phosphorodithioate (malathion), 2-chloro-1-(2,4,5-trichlorophenyl)vinyldimethyl phosphate (tetrachlorvinphos), 2-chloro-1-(2,4-dichlorophenyl) vinyldiethyl phosphate (chlorfenvinphos), O,O-dimethyl-O-p-cyanophenyl phosphorothioate (cyanophos), O,S-dimethyl-N-acetyl phosphoroamidethioate (acephate), O,O-diethyl-O-(5-phenyl-3-isoxazolyl) phosphorothioate (isoxathion), O-ethyl-O-2-isopropoxycarbonylphenyl-N-isopropyl phosphoroamidethioate (isofenphos), O,O,O',O'-tetraethyl-S,S'-methylene diphosphorodithioate (ethion), O,O-diethyl-S-2-ethylthioethyl phosphorodithioate (ethylthiometon), O-6-ethoxy-2-ethylpyrimidin-4-yl-O,O-dimethyl phosphorothioate (etrimfos), O,O-diethyl-O-quinoxatine-2-yl phosphorothioate (quinalphos), O,O-diethyl-O-3,5,6-trichloro-2-pyridyl phosphorothioate (chlorpyrifos), O,O-dimethyl-O-3,5,6-trichloro-2-pyridyl phosphorothioate (chlorpyrifosmethyl), 2-chloro-1-(2,4-dichlorophenyl)vinyldimethyl phosphate (demethylvinphos), O,O-dimethyl-S-(N-methylcarbamoylmethyl) phosphorodithioate (dimethoate), O-ethyl-O-4-methylthiophenyl-S-propyl phosphorodithioate (sulprofos), O,O-diethyl-O-2-isopropyl-6-methylpyrimidin-4-yl phosphorothioate (diazinon), O,O-dimethyl-S-ethylthioethyl phosphorodithioate (thiometon), O,O-dimethyl-S-2-(1-methylcarbamoylethylthio)ethyl phosphorodithioate (vamidothion), (RS)-O-1-(4-chlorophenyl)pyrazol-4-yl-O-ethyl-S-n-propyl phosphorothioate (pyraclofos), O,O-diethyl-O-(3-oxo-2-phenyl-2H-pyridazin-6-yl phosphorothioate (pyridaphenthion), O-2-diethylamino-6-methylpyrimidin-4-yl-O,O-dimethyl phosphorothioate (pirimiphos-methyl), 2-methoxy-4H-1,3,2-benzodioxaphosphorine-2-sulfide (salithion), dimethylethylsulfinylisopropyl thiophosphate (ESP), O,O-dimethyl-O-{3-methyl-4-(methylthio)phenyl} thiophosphate (fenthion), ethyldimethyldithiophosphorylphenylacetate (phenthoate), 3-(dimethoxyphosphinyloxy)-N-methyl-cis-crotonamide (monocrotophos), O,S-dimethyl phosphoramidothioate (methamidophos), O-1-phenyl-1H-1,2,4-triazol-3-yl phosphorothioate (triazophos) and the like; preferably isoxathion, diazinon, prothiofos, methidathion, thiometon, malathion, quinalphos and dimethoate.

The preferred ratio of the active ingredients of the present invention is 1 to 50 parts by weight of the active ingredient (s) of formula (I) to 1 part by weight of pyrimidifen, preferably 5 to 35 parts by weight of the compound(s) of formula (I) to 1 part by weight of pyrimidifen.

The total active ingredient content of the compositions is generally in the region of 1 to 50% by weight in liquid formulations, 0.1 to 25% by weight in dusts, 1 to 90% by weight in wettable powders, and 0.1 to 25% by weight in granules. However, other suitable compositions will be apparent to those skilled in the art, according to the conditions of use, as well as other determining factors.

The active ingredients of the present invention may suitably be mixed with an adjuvant useful in agricultural or horticultural preparations. Pyrimidifen and the active organic phosphates of formula (I) may be prepared by well-known means in the form of, for example, undiluted emulsifiable concentrates, pastes for spraying, solutions for spraying or diluting, diluted emulsifiable concentrates, water-soluble powders, dusts, granules, flowable formulations, dry flowable formulations, smoking formulations, fumigating formulations or capsules using, for example, polymer material for the capsule.

In order to prepare solid formulations, additives and/or carriers may be used and suitable examples include: vegetable powders, such as soybean flour or wheat flour; mineral microcrystalline powders, such as diatomaceous earth, apatite, plaster, talc, bentonite or clay; and organic or inorganic substances, such as sodium benzoate, urea, sodium sulfate and the like.

Suitable solvents for use in the preparation of liquid formulations of the present invention include: vegetable oils; mineral oils; petroleum products, including kerosine, xylene and solvent naphtha; cyclohexane, cyclohexanone, dimethylformamide, dimethylsulfoxide, trichloroethylene, methyl isobutyl ketone, water and the like. Further, in order to improve the homogeity and stability of the formulation, if necessary, surface active agents can be added.

Wettable powders, emulsifiable concentrates, aqueous solutions, flowable formulations and dry flowable formulations, prepared as described above, may be applied to plants in the form of an aqueous suspension or emulsion after dilution to a prescribed concentration with water. Powders or granules are generally applied without dilution.

The compositions of the present invention exhibit excellent synergistic acaricidal effects far beyond the additive effect of either component separately, so that it is correspondingly possible to decrease the amount of active ingredients used.

The pesticidal, and generally insecticidal and acaricidal, compositions of the present invention are effective against harmful insect pests, such as; the citrus red mite (*Panonychus citri*), the pink citrus rust mite (*Aculops pelekassi*), the European red mite (*Panonychus ulmi*), the hawthorn spider mite (*Tetranychus vinnensis*) and the two-spotted spider mite (*Tetranychus urticae*) which are harmful to fruit trees such as the mandarin orange, apple and peach trees, as well as grape vines. In addition, the compositions of the present invention are useful against the kanzawa spider mite (Tetranychus kanzawai), which is harmful to tea trees, and the carmine spider mite (*Tetranychus cinnabarinus*) which is harmful to vegetables, eggplants, watermelons and melons.

The compositions of the present invention are useful not only against the foregoing pests, but they are also useful against such pests as: tortricids; aphids, such as tropical citrus aphid, apple aphid, and apple leafcurl aphid; and scales, such as arrowhead scale and indian wax scale, which are harmful to fruit trees such as mandarin orange and apple trees. The tortricids, scales such as white peach scale, and mugwort looper are harmful to tea trees, and are treatable by the compositions of the present invention.

Although the mechanism of the synergistic effect shown by the compositions of the present invention is not yet clear, it may well be that organic phosphates are capable of inhibiting the enzymatic detoxification and catabolism of pyrimidifen in the appropriate pests, particularly mites, which have low sensitivity to pyrimidifen.

The present invention will now be further illustrated by way of the following non-limiting Examples, wherein percentages and ratios are by weight, unless otherwise specified. Where Pyrimidifen is used in the following Examples, it was prepared in accordance with the procedures disclosed in EP-A-196,524.

Formulation Example 1

An emulsifiable concentrate was obtained by mixing parts of pyrimidifen, 50 parts of isoxathion, 20 parts of Paracol KPS (Nippon Nyukazai Co., Ltd., a combined emulsifier) and 26 parts of xylene.

Formulation Example 2

An emulsifiable concentrate was obtained by mixing 4 parts of pyrimidifen, 43 parts of thiometon concentrate (containing 60% active ingredient), 8 parts of Emulsifier AC 260 (Sandoz Co., Ltd., a combined emulsifier) and 45 parts of xylene.

Formulation Example 3

A wettable powder formulation was obtained by mixing 4 parts of pyrimidifen, 34 parts of diazinon, 2 parts of Neogen Powder (Dai-ichi Kogyo Seiyaku Co., Ltd., sodium dodecylbenzenesulfonate), 10 parts of magnesium carbonate T (Tokuyama Soda Co., Ltd.), 12 parts of Carplex #80 (Shionogi Seiyaku Co., Ltd., amorphous silicon dioxide), 12 parts of Carplex #1120 (Shionogi Seiyaku Co., Ltd., amorphous silicon dioxide) and 23 parts of calcium carbonate powder, and pulverising the resulting mix with a Jet-O-Mizer (Seishin Enterprise Co., Ltd., Japan).

Formulation Example 4

The constituents used for a flowable formulation, were as follows:
1) Four parts of pyrimidifen;
2) 40 parts of dimethoate;
3) 1 part of Newcol 291 PG (Nippon Nyukazai Co., Ltd., Japan, sodium diethylhexylsulfosuccinate);
4) 47.7 parts of water;
5) 3 parts of Sunex P 201;
6) 1 part of VeegumR (Sanyo Chemical Industries);
7) 0.3 part of Rhodopol 23 (Rhone-Poulenc); and
8) 10 parts of ethyleneglycol.

Constituents 3) and 5) were dissolved in 40 parts of water. 1) and 2) were then added to the resulting solution and the whole was pulverized using an Attritor (Mitsui Miike Engineering Corp., Japan). Separately, the remaining 7.7 parts of water were mixed with 8), and 6) and 7) were added to the resulting solution. A flowable formulation was obtained from a combination of the two preparations thus obtained.

Formulation Example 5

An emulsifiable concentrate was obtained by mixing 4 parts of pyrimidifen, 50 parts of ethion (Tomoho Agrica Co., Ltd., Japan), 20 parts of Paracol KPS (Nippon Nyukazai Co., Ltd., Japan, a combined emulsifier) and 26 parts of xylene.

Formulation Example 6

An emulsifiable concentrate was obtained by mixing parts of pyrimidifen, 40 parts of profenofos (Nihon Nohyaku Co., Ltd., Japan), 20 parts of Paracol KPS (Nippon Nyukazai Co., Ltd., Japan, a combined emulsifier) and 36 parts of xylene.

Formulation Example 7

A wettable powder formulation was obtained by mixing 4 parts of pyrimidifen, 40 parts of chlorpyrifos (Nissan Chemical Industries, Ltd., Japan), 5 parts of Neogen Powder (Dai-ichi Kogyo Seiyaku Co., Ltd., Japan, sodium dodecylbenzenesulfonate) and 51 parts of Kaolinite Clay (Georgia Kaolin Co., Inc.), and pulverising the resulting mix with a Jet-O-Mizer.

Formulation Example 8

A wettable powder formulation was obtained by mixing 4 parts of pyrimidifen, 40 parts of monocrotophos (Nihon Nohyaku Co., Ltd., Japan), 5 parts of Neogen Powder (Dai-ichi Kogyo Seiyaku Co., Ltd., Japan, sodium dodecylbenzenesulfonate) and 51 parts of Kaolinite Clay (Georgia Kaolin Co., Inc.), followed by pulverizing by use of Jet-O-Mizer.

Formulation Reference Example

A wettable powder containing 4% pyrimidifen was obtained by mixing 4 parts of pyrimidifen, 84 parts of clay, 1 part of Newcol 291 PG, 1 part of Carplex #80 and 10 parts of Lavelin FAN (Dai-ichi Kogyo Co., Ltd., Japan, sodium salt of naphthalenesulfonic acid condensate), and pulverising the resulting mix using a Jet-O-Mizer.

The following Test Examples illustrate the pesticidal effects of the compositions of the present invention.

Test Example 1

Cidal Effect on Citrus Red Mites from the Shizuoka Prefecture

A sponge plate of 1 cm thickness and saturated with water was placed in a Petri dish 9 cm in diameter, and the Petri dish was covered with a filter paper. A piece of mulbery leaf 13 cm$^2$ in size was laid on the filter paper, and then 25 to 35 female adult citrus red mites were inoculated onto the leaf using a small writing brush. After the mites had stopped moving, test solutions of pesticide diluted to specific concentrations with water were sprayed onto the mites. The test preparations used were as follows:

The wettable powder formulation of pyrimidifen mentioned in Formulation Reference Example 1;
Karphos emulsifiable concentrate (containing isoxathion by 50%, Sankyo Co., Ltd., Japan);
Diazinon emulsifiable concentrate (containing diazinon by 40%, Sankyo Co., Ltd., Japan);
Tokuthion emulsifiable concentrate (containing prothiofos by 45%, Japan Bayer Agrochem. Co., Ltd., Japan);
Supracide emulsifiable concentrate (containing methidathion by 40%, Nihon Nohyaku Co., Ltd., Japan);
Ekatin emulsifiable concentrate (containing thiometon by 25%, Sankyo Co., Ltd., Japan);
Malathon emulsifiable concentrate (containing malathion by 50%, Sankyo Co., Ltd., Japan);
Ekalux emulsifiable concentrate (containing quinalphos by 40%, Sankyo Co., Ltd., Japan); and Dimethoate emulsifiable concentrate (containing dimethoate by 43%, Kyushu Sankyo Co., Ltd., Japan).

The sample solutions were sprayed onto the leaf sections at a dose of 7 ml each from a rotary spraying tower of the Mizuho-type. After the test solutions had been applied, the leaf samples were allowed to stand in a thermostatic room at 25° C. and 60% humidity. After 3 days under these conditions, mortality was determined, and the results are shown in Table 1. Mortality was calculated from the numbers of dead mites, including mites in evident agony.

TABLE 1

| Pesticide Combination | Concn (ppm) | Mortality (%) |
|---|---|---|
| Pyrimidifen + isoxathion | 13 + 330 | 100 |
| Pyrimidifen + isoxathion | 6.5 + 165 | 100 |
| Pyrimidifen + isoxathion | 3.3 + 83 | 90 |
| Pyrimidifen + diazinon | 13 + 200 | 100 |
| Pyrimidifen + diazinon | 6.5 + 100 | 85 |
| Pyrimidifen + prothiofos | 13 + 450 | 100 |
| Pyrimidifen + prothiofos | 6.5 + 225 | 91 |
| Pyrimidifen + methidathion | 13 + 200 | 100 |
| Pyrimidifen + methidathion | 6.5 + 100 | 80 |
| Pyrimidifen + thiometon | 13 + 125 | 100 |
| Pyrimidifen + thiometon | 6.5 + 63 | 85 |
| Pyrimidifen + malathion | 13 + 250 | 100 |
| Pyrimidifen + malathion | 6.5 + 125 | 80 |
| Pyrimidifen + quinalphos | 13 + 400 | 100 |
| Pyrimidifen + quinalphos | 6.5 + 200 | 100 |
| Pyrimidifen + dimethoate | 13 + 430 | 100 |
| Pyrimidifen + dimethoate | 6.5 + 215 | 80 |
| Pyrimidifen | 13 | 60 |
| Pyrimidifen | 6.5 | 24 |
| Pyrimidifen | 3.3 | 15 |
| Isoxathion | 330 | 80 |
| Isoxathion | 165 | 60 |
| Isoxathion | 83 | 30 |
| Diazinon | 200 | 50 |
| Diazinon | 100 | 40 |
| Prothiofos | 450 | 60 |
| Prothiofos | 225 | 7 |
| Methidathion | 200 | 30 |
| Methidathion | 100 | 14 |
| Thiometon | 125 | 26 |
| Thiometon | 63 | 23 |
| Malathion | 250 | 30 |
| Malathion | 125 | 26 |
| Quinalphos | 400 | 80 |
| Quinalphos | 200 | 70 |
| Dimethoate | 430 | 60 |
| Dimethoate | 215 | 51 |

Test Example 2

Cidal Effect on Citrus Red Mites from the Nagasaki Prefecture

This test was performed following a procedure similar to that of Test Example 1, but using citrus red mites from the Nagasaki Prefecture origin rather than from the Shizuoka Prefecture. The results are shown in Table 2.

TABLE 2

| Pesticide Combination | Concn (ppm) | Mortality (%) |
|---|---|---|
| Pyrimidifen + isoxathion | 20 + 500 | 100 |
| Pyrimidifen + diazinon | 20 + 400 | 100 |
| Pyrimidifen + prothiofos | 20 + 450 | 100 |
| Pyrimidifen + methidathion | 20 + 400 | 100 |
| Pyrimidifen + thiometon | 20 + 250 | 100 |
| Pyrimidifen + malathion | 20 + 500 | 100 |
| Pyrimidifen + quinalphos | 20 + 400 | 100 |
| Pyrimidifen | 20 | 52 |
| Isoxathion | 500 | 54 |
| Diazinon | 400 | 75 |
| Prothiofos | 450 | 67 |
| Methidathion | 400 | 11 |
| Thiometon | 250 | 0 |
| Malathion | 500 | 14 |
| Quinalphos | 400 | 80 |

What is claimed is:

1. A miticidal composition comprising a synergistic insecticidally effective amount of a mixture of 1:20 to 1:33 of pyrimidifen to quinalphos.

2. A method for the treatment of an agricultural area against mites comprising administering thereto a synergistic insecticidally effective amount of the composition of claim 1.

3. A method for the treatment of vegetative reproductive material to protect against mites comprising administering thereto a synergistic insecticidally effective amount of the composition of claim 1.

* * * * *